US009962188B2

(12) United States Patent
Milella, Jr. et al.

(10) Patent No.: US 9,962,188 B2
(45) Date of Patent: May 8, 2018

(54) EXTERNAL FIXATION SYSTEM AND METHODS OF USE

(71) Applicant: Cardinal Health 247. Inc., Dublin, OH (US)

(72) Inventors: Michael J. Milella, Jr., Richmond, IL (US); John P. Marotta, Denver, CO (US); Justin Rhett Taber, Lafayette, CO (US); Katy Ren'e Swanson, Englewood, CO (US); Sarah E. Schaake, Denver, CO (US)

(73) Assignee: Cardinal Health 247. Inc., Dublin, OH (US)

( * ) Notice: Subject to any disclaimer, the term of this patent is extended or adjusted under 35 U.S.C. 154(b) by 170 days.

(21) Appl. No.: 14/066,274

(22) Filed: Oct. 29, 2013

(65) Prior Publication Data
US 2015/0119886 A1    Apr. 30, 2015

(51) Int. Cl.
*A61B 17/00* (2006.01)
*A61F 4/00* (2006.01)
*A61F 5/04* (2006.01)
*A61B 17/64* (2006.01)

(52) U.S. Cl.
CPC .................. *A61B 17/6466* (2013.01)

(58) Field of Classification Search
CPC ............ A61B 17/6466; A61B 17/6475; A61B 17/6483; A61B 17/6491
USPC ..................................................... 606/54–59
See application file for complete search history.

(56) References Cited

U.S. PATENT DOCUMENTS

| | | |
|---|---|---|
| 4,098,269 A | 7/1978 | Judet |
| 4,244,360 A | 1/1981 | Dohogne |
| 4,273,116 A | 6/1981 | Chiquet |
| 4,360,012 A | 11/1982 | McHarrie et al. |
| 4,393,868 A | 7/1983 | Teague |
| 4,456,004 A | 6/1984 | Kenny |
| 4,475,546 A | 10/1984 | Patton |
| 4,483,334 A | 11/1984 | Murray |
| 4,488,542 A | 12/1984 | Helland |
| 4,502,473 A | 3/1985 | Harris et al. |
| 4,541,422 A | 9/1985 | de Zbikowski |
| 4,554,915 A | 11/1985 | Brumfield |
| 4,564,007 A | 1/1986 | Coombs et al. |
| 4,576,158 A | 3/1986 | Boland |
| 4,584,995 A | 4/1986 | Koeneman |
| 4,600,000 A | 7/1986 | Edwards |
| 4,604,997 A | 8/1986 | De Bastiani et al. |

(Continued)

OTHER PUBLICATIONS

International Search Report and Written Opinion for Application No. PCT/US2014/062678, dated Jan. 20, 2015, 9 pages.

*Primary Examiner* — Ellen C Hammond
*Assistant Examiner* — Christina Negrellirodriguez
(74) *Attorney, Agent, or Firm* — Adnan H. Bohri

(57) ABSTRACT

A clamp system includes a first clamp, a second clamp, and a fixation rod. The first clamp at least partially defines a first jaw for receiving a support rod and a central opening. The second clamp at least partially defines a second jaw for receiving a pin and a central opening. At least one of the first clamp and the second clamp comprises a boss for rotatably positioning the first clamp relative to the second clamp. The fixation rod is received in the central openings of the first clamp and the second clamp for selectively securing a position of the first clamp relative to the second clamp.

19 Claims, 17 Drawing Sheets

(56) References Cited

U.S. PATENT DOCUMENTS

| | | |
|---|---|---|
| 4,612,921 A | 9/1986 | Lazo de Zbikowski |
| 4,620,533 A | 11/1986 | Mears |
| 4,621,627 A | 11/1986 | DeBastiani et al. |
| 4,624,249 A | 11/1986 | Alvarez Cambras |
| 4,628,919 A | 12/1986 | Clyburn |
| 4,628,921 A | 12/1986 | Rousso |
| 4,662,365 A | 5/1987 | Gotzen et al. |
| 4,696,293 A | 9/1987 | Ciullo |
| 4,730,608 A | 3/1988 | Schlein |
| 4,747,400 A | 5/1988 | Koeneman et al. |
| 4,757,809 A | 7/1988 | Koeneman et al. |
| 4,784,125 A | 11/1988 | Monticelli et al. |
| 4,848,368 A | 7/1989 | Kronner |
| D303,577 S | 9/1989 | Hammer |
| 4,889,111 A | 12/1989 | Ben-Dov |
| 4,890,631 A | 1/1990 | Hardy |
| 4,893,618 A | 1/1990 | Herzberg |
| 4,895,141 A | 1/1990 | Koeneman et al. |
| 4,919,119 A | 4/1990 | Jonsson et al. |
| 4,920,959 A | 5/1990 | Witzel et al. |
| 4,936,843 A | 6/1990 | Sohngen |
| 4,968,316 A | 11/1990 | Hergenroeder |
| 4,969,886 A | 11/1990 | Cziffer et al. |
| 4,998,935 A | 3/1991 | Pennig |
| 5,021,054 A | 6/1991 | Monfardini et al. |
| 5,024,618 A | 6/1991 | Tepic |
| 5,057,113 A | 10/1991 | Mingozzi |
| 5,067,954 A | 11/1991 | Ilizarov |
| 5,074,866 A | 12/1991 | Sherman et al. |
| 5,080,661 A | 1/1992 | Lavender et al. |
| 5,092,866 A | 3/1992 | Breard |
| 5,122,140 A | 6/1992 | Asche et al. |
| 5,196,012 A | 3/1993 | Malka |
| 5,207,676 A | 5/1993 | Canadell et al. |
| 5,275,599 A | 1/1994 | Zbikowski et al. |
| 5,292,322 A | 3/1994 | Faccioli et al. |
| 5,304,177 A | 4/1994 | Pennig |
| 5,312,403 A | 5/1994 | Frigg |
| 5,320,623 A | 6/1994 | Pennig |
| 5,342,360 A | 8/1994 | Faccioli et al. |
| 5,358,504 A | 10/1994 | Paley et al. |
| 5,391,167 A | 2/1995 | Pong et al. |
| 5,397,322 A | 3/1995 | Campopiano |
| 5,403,313 A | 4/1995 | Lin |
| 5,405,347 A | 4/1995 | Lee et al. |
| 5,437,666 A | 8/1995 | Tepic et al. |
| 5,437,667 A | 8/1995 | Papierski et al. |
| 5,437,668 A | 8/1995 | Aronson et al. |
| 5,443,464 A | 8/1995 | Russell et al. |
| 5,443,465 A | 8/1995 | Pennig |
| 5,451,225 A | 9/1995 | Ross, Jr. et al. |
| 5,451,226 A | 9/1995 | Pfeil et al. |
| 5,454,810 A | 10/1995 | Pohl et al. |
| 5,545,162 A | 8/1996 | Huebner |
| 5,578,041 A | 11/1996 | Nash et al. |
| 5,591,164 A | 1/1997 | Nazre et al. |
| 5,601,550 A | 2/1997 | Esser |
| 5,624,440 A | 4/1997 | Huebner |
| 5,630,814 A | 5/1997 | Ross, Jr. et al. |
| 5,630,815 A | 5/1997 | Pohl et al. |
| 5,653,707 A | 8/1997 | Taylor et al. |
| 5,658,283 A | 8/1997 | Huebner |
| 5,662,648 A | 9/1997 | Faccioli et al. |
| 5,662,649 A | 9/1997 | Huebner |
| 5,674,221 A | 10/1997 | Hein et al. |
| 5,676,664 A | 10/1997 | Allard et al. |
| 5,681,309 A | 10/1997 | Ross, Jr. et al. |
| 5,683,389 A | 11/1997 | Orsak |
| 5,688,271 A | 11/1997 | Faccioli et al. |
| 5,690,633 A | 11/1997 | Taylor et al. |
| 5,695,496 A | 12/1997 | Orsak |
| 5,709,681 A | 1/1998 | Pennig |
| 5,725,526 A | 3/1998 | Allard et al. |
| 5,728,095 A | 3/1998 | Taylor et al. |
| 5,738,684 A | 4/1998 | Thomas et al. |
| 5,741,252 A * | 4/1998 | Mazzio ............... A61B 17/62 |
| | | 606/54 |
| 5,746,741 A | 5/1998 | Kraus et al. |
| 5,752,954 A | 5/1998 | Mata et al. |
| 5,766,173 A | 6/1998 | Ross, Jr. et al. |
| 5,769,851 A | 6/1998 | Veith |
| 5,776,132 A | 7/1998 | Blyakher |
| 5,788,695 A | 8/1998 | Richardson |
| 5,792,076 A | 8/1998 | Orsak et al. |
| 5,797,908 A | 8/1998 | Meyers et al. |
| 5,803,924 A | 9/1998 | Oni et al. |
| 5,827,282 A | 10/1998 | Pennig |
| 5,827,284 A | 10/1998 | Weigum et al. |
| 5,843,081 A | 12/1998 | Richardson et al. |
| 5,863,292 A | 1/1999 | Tosic |
| 5,885,282 A | 3/1999 | Szabo |
| 5,891,144 A | 4/1999 | Mate et al. |
| RE36,221 E | 6/1999 | Breard |
| 5,921,985 A | 7/1999 | Ross, Jr. et al. |
| 5,928,230 A | 7/1999 | Tosic |
| 5,928,234 A | 7/1999 | Manspeizer |
| 5,931,837 A | 8/1999 | Marsh et al. |
| 5,944,719 A | 8/1999 | Leban |
| 5,961,515 A | 10/1999 | Taylor et al. |
| 5,968,043 A | 10/1999 | Ross, Jr. et al. |
| 5,971,984 A | 10/1999 | Taylor et al. |
| 5,976,133 A | 11/1999 | Kraus et al. |
| 5,976,134 A | 11/1999 | Huebner |
| 5,997,537 A | 12/1999 | Walulik |
| 6,010,501 A | 1/2000 | Raskin et al. |
| 6,030,386 A | 2/2000 | Taylor et al. |
| 6,036,691 A | 3/2000 | Richardson |
| 6,053,915 A | 4/2000 | Bruchmann |
| 6,080,153 A | 6/2000 | Mata et al. |
| 6,129,727 A | 10/2000 | Austin |
| 6,152,925 A | 11/2000 | Marsh et al. |
| 6,159,210 A | 12/2000 | Voor |
| 6,162,222 A | 12/2000 | Poke et al. |
| 6,162,223 A | 12/2000 | Orsak et al. |
| 6,162,224 A | 12/2000 | Huebner |
| 6,171,308 B1 | 1/2001 | Bailey et al. |
| 6,171,309 B1 | 1/2001 | Huebner |
| 6,197,027 B1 | 3/2001 | Hajianpour |
| 6,221,072 B1 | 4/2001 | Termaten |
| 6,245,071 B1 | 6/2001 | Pierson |
| 6,277,118 B1 | 8/2001 | Grant et al. |
| 6,277,119 B1 | 8/2001 | Walulik et al. |
| 6,340,361 B1 | 1/2002 | Kraus et al. |
| 6,342,054 B1 | 1/2002 | Mata |
| 6,423,061 B1 | 7/2002 | Bryant |
| 6,423,062 B2 | 7/2002 | Enayati |
| 6,461,358 B1 | 10/2002 | Faccioli et al. |
| 6,482,206 B2 | 11/2002 | Schoenefeld |
| 6,491,694 B1 | 12/2002 | Orsak |
| 6,514,254 B1 | 2/2003 | Falls |
| 6,520,961 B1 | 2/2003 | Marsh |
| 6,530,925 B2 | 3/2003 | Boudard et al. |
| 6,537,274 B1 | 3/2003 | Katz |
| 6,537,275 B2 | 3/2003 | Venturini et al. |
| 6,565,564 B2 | 5/2003 | Hoffman et al. |
| 6,575,972 B1 | 6/2003 | Gordon |
| 6,585,736 B2 | 7/2003 | Hajianpour |
| 6,613,049 B2 | 9/2003 | Winquist et al. |
| 6,616,664 B2 | 9/2003 | Walulik et al. |
| 6,652,523 B1 | 11/2003 | Evrard et al. |
| 6,652,524 B1 | 11/2003 | Weiner |
| 6,678,562 B1 | 1/2004 | Tepper |
| 6,702,814 B2 | 3/2004 | Walulik et al. |
| 6,716,212 B1 | 4/2004 | Pickens |
| 6,730,086 B2 | 5/2004 | Hehli et al. |
| 6,746,448 B2 | 6/2004 | Weiner et al. |
| 6,793,655 B2 | 9/2004 | Orsak |
| 6,840,939 B2 | 1/2005 | Venturini et al. |
| 6,860,883 B2 | 3/2005 | Janowski et al. |
| 7,004,943 B2 | 2/2006 | Ferrante et al. |
| 7,033,392 B2 | 4/2006 | Schmiel et al. |
| 7,041,103 B2 | 5/2006 | Hoffmann et al. |
| 7,048,735 B2 | 5/2006 | Ferrante et al. |
| 7,147,639 B2 | 12/2006 | Berki et al. |

(56) References Cited

U.S. PATENT DOCUMENTS

| | | |
|---|---|---|
| 7,153,302 B1 | 12/2006 | Hajianpour |
| 7,169,149 B1 | 1/2007 | Hajianpour |
| 7,226,449 B2 | 6/2007 | Venturini et al. |
| 7,241,074 B2 | 7/2007 | Thomke et al. |
| 7,252,669 B1 | 8/2007 | McIntyre |
| 7,282,052 B2 | 10/2007 | Mullaney |
| 7,291,148 B2 | 11/2007 | Agee et al. |
| 7,306,601 B2 | 12/2007 | McGrath et al. |
| 7,361,176 B2 | 4/2008 | Cooper et al. |
| 7,367,977 B2 | 5/2008 | Estrada, Jr. |
| 7,422,593 B2 | 9/2008 | Cresina et al. |
| 7,449,023 B2 | 11/2008 | Walulik et al. |
| 7,465,303 B2 | 12/2008 | Riccione et al. |
| 7,479,142 B2 | 1/2009 | Weiner et al. |
| 7,491,008 B2 | 2/2009 | Thomke et al. |
| 7,527,626 B2 | 5/2009 | Lutz et al. |
| 7,608,074 B2 | 10/2009 | Austin et al. |
| 7,632,271 B2 | 12/2009 | Baumgartner et al. |
| 7,645,279 B1 | 1/2010 | Haupt |
| 7,666,212 B2 | 2/2010 | Pathak |
| 7,708,736 B2 | 5/2010 | Mullaney |
| 7,722,609 B2 | 5/2010 | Bordeaux |
| 7,749,224 B2 | 7/2010 | Cresina et al. |
| 7,828,801 B2 | 11/2010 | Mirza et al. |
| 7,841,998 B2 | 11/2010 | Pomeroy et al. |
| 7,887,495 B2 | 2/2011 | Boyd et al. |
| 7,887,537 B2 | 2/2011 | Ferrante et al. |
| 7,931,650 B2 | 4/2011 | Winquist et al. |
| 7,931,651 B2 | 4/2011 | Webb et al. |
| 7,938,829 B2 | 5/2011 | Mullaney |
| 7,955,333 B2 | 6/2011 | Yeager |
| 7,955,334 B2 | 6/2011 | Steiner et al. |
| 7,985,221 B2 | 7/2011 | Coull et al. |
| 8,029,505 B2 | 10/2011 | Hearn et al. |
| 8,062,293 B2 | 11/2011 | Steiner et al. |
| 8,075,560 B2 | 12/2011 | Hajianpour |
| 8,083,740 B2 | 12/2011 | Eslami et al. |
| 8,114,077 B2 | 2/2012 | Steiner et al. |
| 8,123,747 B2 | 2/2012 | Hajianpour |
| 8,137,347 B2 | 3/2012 | Weiner et al. |
| 8,147,491 B2 | 4/2012 | Lavi |
| 8,167,880 B2 | 5/2012 | Vasta |
| 8,172,840 B2 | 5/2012 | Mürner et al. |
| 8,182,483 B2 | 5/2012 | Bagnasco et al. |
| 8,187,274 B2 | 5/2012 | Schulze |
| 8,192,434 B2 | 6/2012 | Huebner et al. |
| 8,235,994 B2 | 8/2012 | Hollawell |
| 8,241,285 B2 | 8/2012 | Mullaney |
| 8,246,561 B1 | 8/2012 | Agee |
| 8,257,353 B2 | 9/2012 | Wong |
| 8,262,656 B2 | 9/2012 | Mirza et al. |
| 8,277,448 B2 | 10/2012 | Daluiski et al. |
| 8,277,449 B2 | 10/2012 | Tan |
| 8,282,636 B2 | 10/2012 | Tan |
| 8,303,587 B2 | 11/2012 | Lehmann et al. |
| 8,323,281 B2 | 12/2012 | Hotchkiss et al. |
| 8,333,766 B2 | 12/2012 | Edelhauser et al. |
| 8,361,073 B2 | 1/2013 | Mullaney |
| 8,366,710 B2 | 2/2013 | Hirata et al. |
| 8,372,073 B2 | 2/2013 | Hoffman et al. |
| 8,382,755 B2 | 2/2013 | Austin et al. |
| 8,403,928 B2 | 3/2013 | Bordeaux |
| 8,419,733 B2 | 4/2013 | Hajianpour |
| 8,439,914 B2 | 5/2013 | Ross et al. |
| 8,444,644 B2 | 5/2013 | Ross et al. |
| 8,454,603 B2 | 6/2013 | Webb et al. |
| 8,454,604 B2 | 6/2013 | Wong |
| 8,486,068 B2 | 7/2013 | Starr |
| 8,486,069 B2 | 7/2013 | Hollawell |
| 8,518,039 B2 | 8/2013 | Mirza et al. |
| 8,523,858 B2 | 9/2013 | Lessig et al. |
| 8,540,713 B2 | 9/2013 | Zandona et al. |
| 8,574,232 B1 | 11/2013 | Ross et al. |
| 2002/0042613 A1 | 4/2002 | Mata |
| 2003/0187432 A1 | 10/2003 | Johnson et al. |
| 2003/0216734 A1 | 11/2003 | Mingozzi et al. |
| 2003/0225405 A1 | 12/2003 | Weiner |
| 2004/0097923 A1 | 5/2004 | Shevlin |
| 2004/0097944 A1 | 5/2004 | Koman et al. |
| 2004/0133199 A1 | 7/2004 | Coati et al. |
| 2004/0133200 A1 | 7/2004 | Ruch et al. |
| 2004/0181221 A1 | 9/2004 | Huebner et al. |
| 2005/0015087 A1 | 1/2005 | Walulik et al. |
| 2005/0043730 A1 | 2/2005 | Janowski et al. |
| 2005/0113829 A1 | 5/2005 | Walulik et al. |
| 2005/0119656 A1 | 6/2005 | Ferrante et al. |
| 2005/0203509 A1 | 9/2005 | Chinnaian et al. |
| 2006/0058797 A1 | 3/2006 | Mathieu et al. |
| 2006/0155276 A1 | 7/2006 | Walulik et al. |
| 2006/0200127 A1 | 9/2006 | Ismail |
| 2006/0235383 A1* | 10/2006 | Hollawell .......... A61B 17/6416 606/54 |
| 2006/0235384 A1 | 10/2006 | Rovesti |
| 2006/0276786 A1 | 12/2006 | Brinker |
| 2006/0287652 A1 | 12/2006 | Lessig et al. |
| 2007/0038217 A1 | 2/2007 | Brown et al. |
| 2007/0055233 A1 | 3/2007 | Brinker |
| 2007/0123856 A1 | 5/2007 | Deffenbaugh et al. |
| 2007/0123858 A1 | 5/2007 | Strub et al. |
| 2008/0195095 A1 | 8/2008 | Renard et al. |
| 2008/0215053 A1 | 9/2008 | Thomke et al. |
| 2008/0221573 A1 | 9/2008 | Kumhyr |
| 2008/0228185 A1 | 9/2008 | Vasta et al. |
| 2008/0255554 A1 | 10/2008 | Richter et al. |
| 2008/0312656 A1 | 12/2008 | Vasta |
| 2009/0036891 A1 | 2/2009 | Brown et al. |
| 2009/0088751 A1 | 4/2009 | Mullaney |
| 2009/0148232 A1 | 6/2009 | Thomke et al. |
| 2009/0198234 A1 | 8/2009 | Knuchel et al. |
| 2009/0222006 A1 | 9/2009 | Allison |
| 2009/0228006 A1 | 9/2009 | Mussolin |
| 2009/0254086 A1 | 10/2009 | Trilla-Muntanola |
| 2009/0264883 A1 | 10/2009 | Steiner et al. |
| 2009/0264884 A1 | 10/2009 | Masse et al. |
| 2010/0042213 A1 | 2/2010 | Nebosky et al. |
| 2010/0179548 A1 | 7/2010 | Marin |
| 2010/0234845 A1 | 9/2010 | Mullaney |
| 2010/0280516 A1 | 11/2010 | Taylor |
| 2010/0298827 A1 | 11/2010 | Cremer et al. |
| 2010/0305568 A1 | 12/2010 | Ross et al. |
| 2011/0082458 A1 | 4/2011 | Crozet et al. |
| 2011/0087226 A1 | 4/2011 | Mürner et al. |
| 2011/0098706 A1 | 4/2011 | Mullaney |
| 2011/0098707 A1 | 4/2011 | Mullaney |
| 2011/0112533 A1 | 5/2011 | Venturini et al. |
| 2011/0144643 A1 | 6/2011 | Lorenz et al. |
| 2011/0172665 A1 | 7/2011 | Winquist et al. |
| 2011/0245830 A1 | 10/2011 | Zgonis et al. |
| 2011/0264094 A1 | 10/2011 | Cunliffe et al. |
| 2011/0288549 A1 | 11/2011 | Steiner et al. |
| 2011/0313418 A1 | 12/2011 | Nikonovas |
| 2011/0313419 A1 | 12/2011 | Mullaney |
| 2012/0004659 A1 | 1/2012 | Miller et al. |
| 2012/0041439 A1 | 2/2012 | Singh et al. |
| 2012/0053584 A1 | 3/2012 | Bütikofer et al. |
| 2012/0078251 A1 | 3/2012 | Benenati et al. |
| 2012/0089142 A1 | 4/2012 | Mullaney et al. |
| 2012/0095462 A1 | 4/2012 | Miller |
| 2012/0123414 A1 | 5/2012 | Steiner et al. |
| 2012/0150180 A1 | 6/2012 | Verma et al. |
| 2012/0150181 A1 | 6/2012 | Dorawa et al. |
| 2012/0150182 A1 | 6/2012 | Dominik et al. |
| 2012/0150183 A1 | 6/2012 | Dorawa et al. |
| 2012/0150184 A1 | 6/2012 | Mullaney |
| 2012/0150185 A1 | 6/2012 | Mullaney |
| 2012/0150186 A1 | 6/2012 | Hajianpour |
| 2012/0184958 A1 | 7/2012 | Knuchel et al. |
| 2012/0203225 A1 | 8/2012 | Mingozzi et al. |
| 2012/0226277 A1 | 9/2012 | Tan et al. |
| 2012/0232554 A1 | 9/2012 | Shaevitz et al. |
| 2012/0289959 A1 | 11/2012 | Miller |
| 2012/0296335 A1 | 11/2012 | Mullaney |
| 2012/0330312 A1 | 12/2012 | Burgherr et al. |
| 2013/0006244 A1 | 1/2013 | Lehmann et al. |

(56) References Cited

U.S. PATENT DOCUMENTS

| | | |
|---|---|---|
| 2013/0018374 A1 | 1/2013 | Edelhauser et al. |
| 2013/0079775 A1 | 3/2013 | Verma et al. |
| 2013/0110110 A1 | 5/2013 | Waisman |
| 2013/0116692 A1 | 5/2013 | Daluiski et al. |
| 2013/0123784 A1 | 5/2013 | Ross et al. |
| 2013/0131676 A1 | 5/2013 | Mullaney |
| 2013/0131677 A1 | 5/2013 | Hoffman et al. |
| 2013/0144289 A1 | 6/2013 | Dorawa |
| 2013/0158551 A1 | 6/2013 | Thomke et al. |
| 2013/0165931 A1 | 6/2013 | Bordeaux |
| 2013/0165932 A1 | 6/2013 | Dominik et al. |
| 2013/0204248 A1 | 8/2013 | Singh et al. |
| 2013/0226179 A1* | 8/2013 | Chreene ............. A61B 17/6466 606/54 |
| 2013/0253512 A1 | 9/2013 | Crozet et al. |
| 2013/0253513 A1 | 9/2013 | Ross et al. |
| 2013/0253514 A1 | 9/2013 | Starr |
| 2013/0267952 A1 | 10/2013 | Webb et al. |
| 2013/0274744 A1 | 10/2013 | Ikemizu |
| 2013/0296858 A1 | 11/2013 | Hollawell |

\* cited by examiner

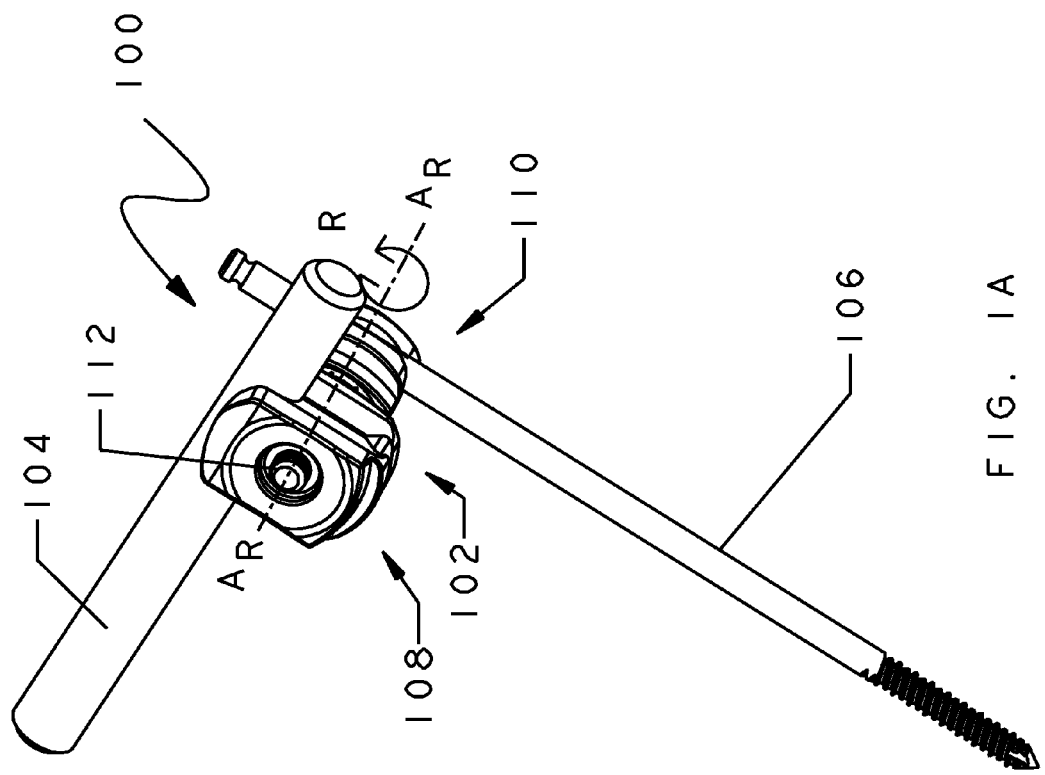

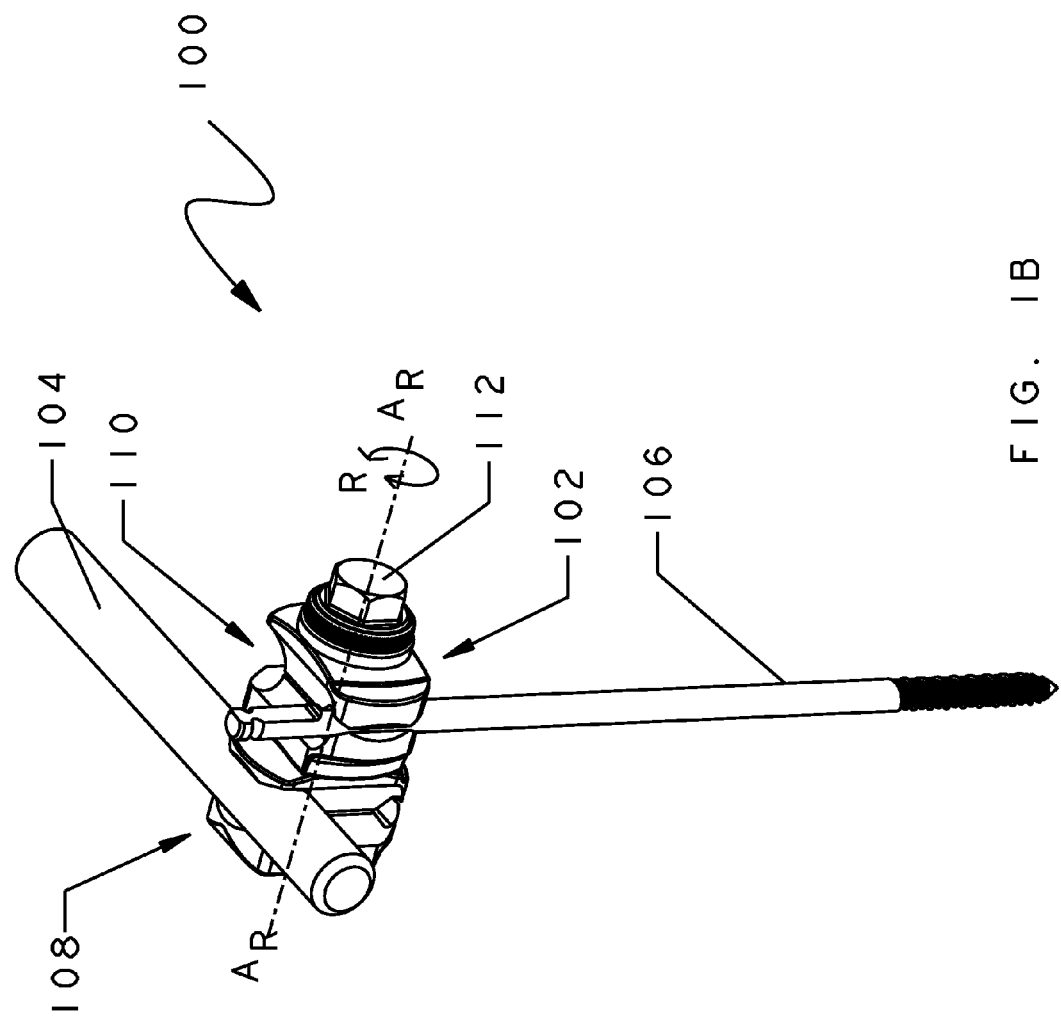

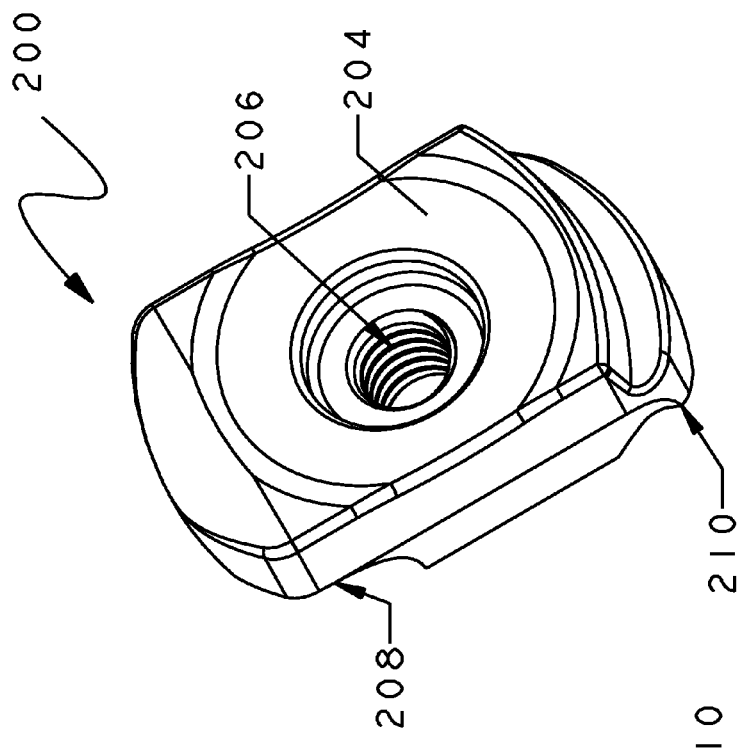
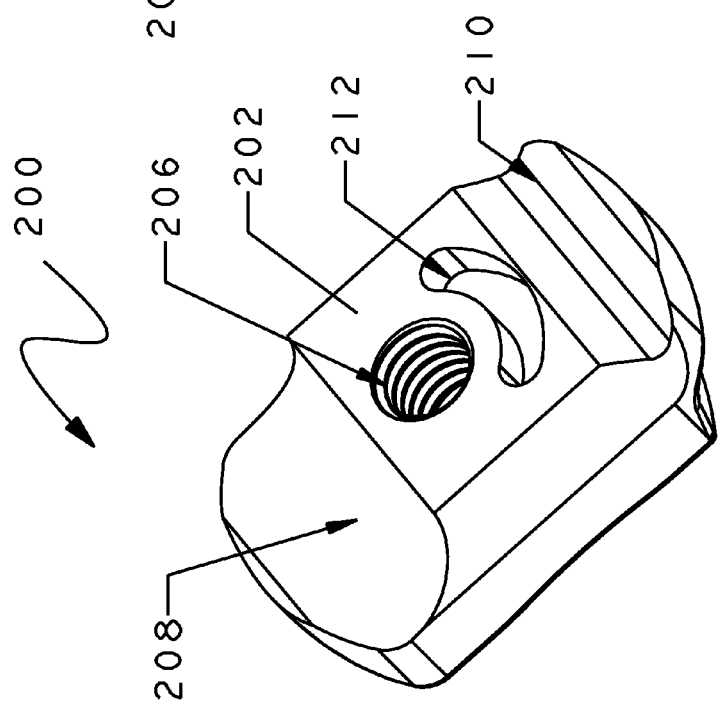

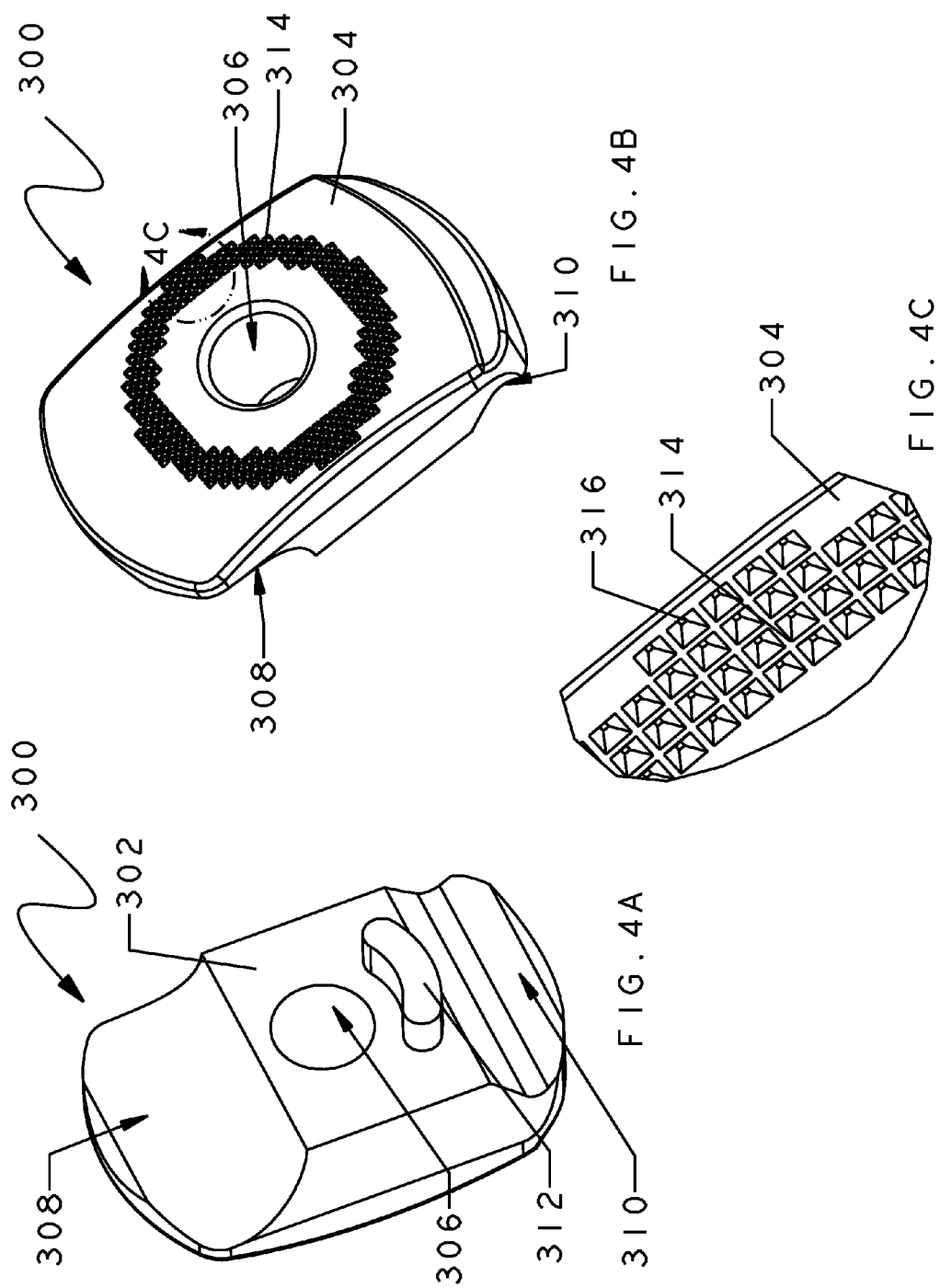

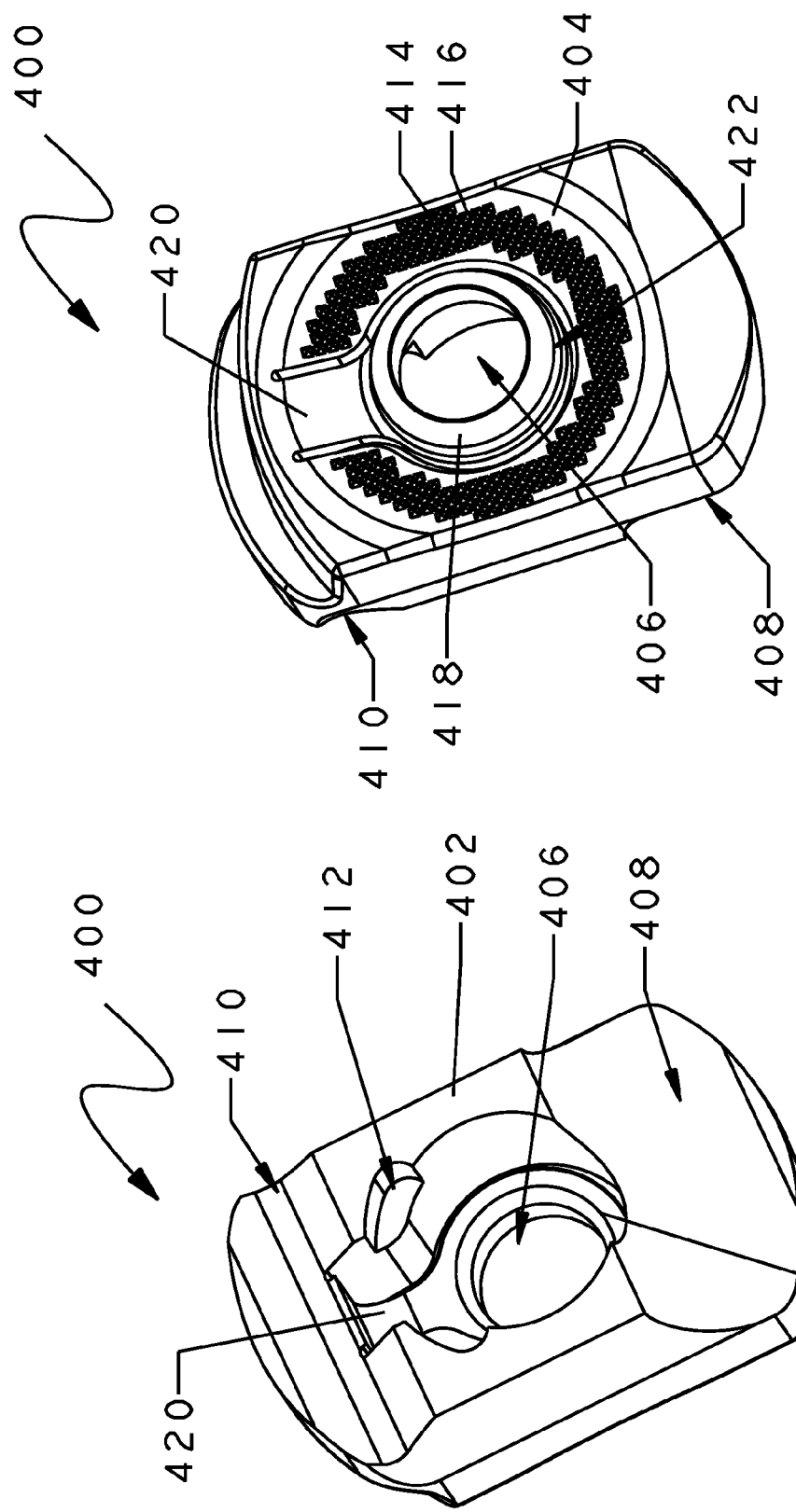

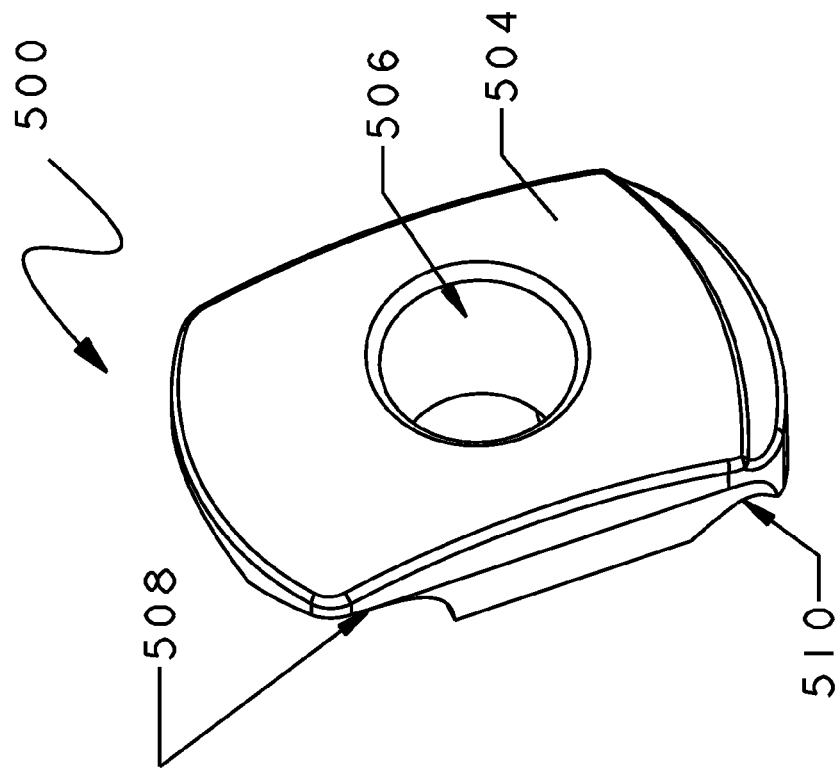
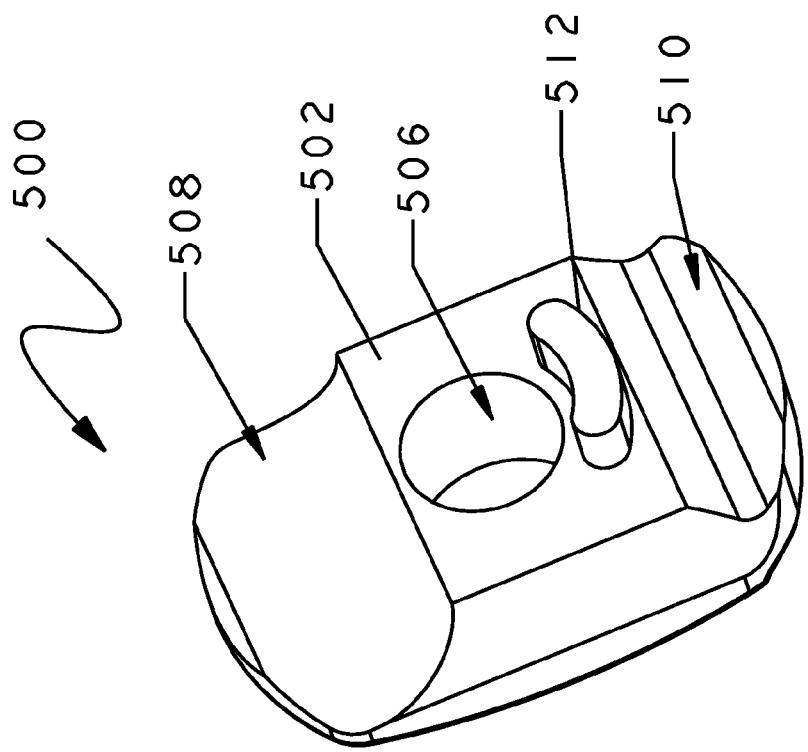
FIG. 6B
FIG. 6A

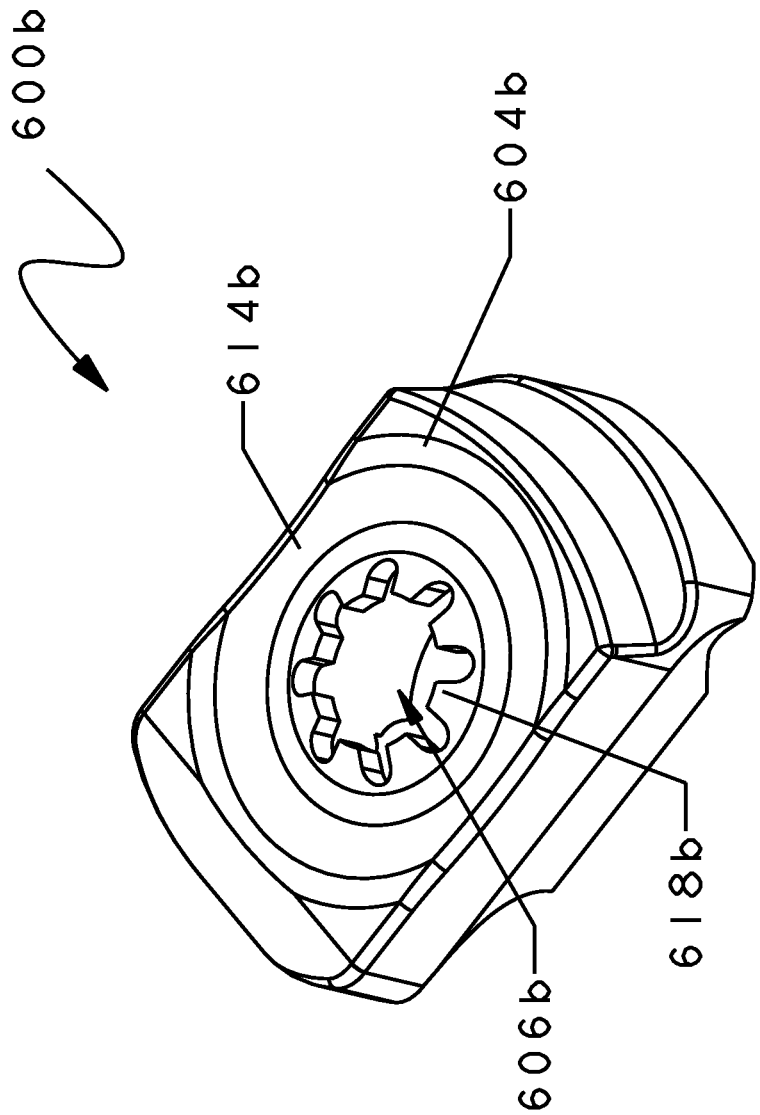

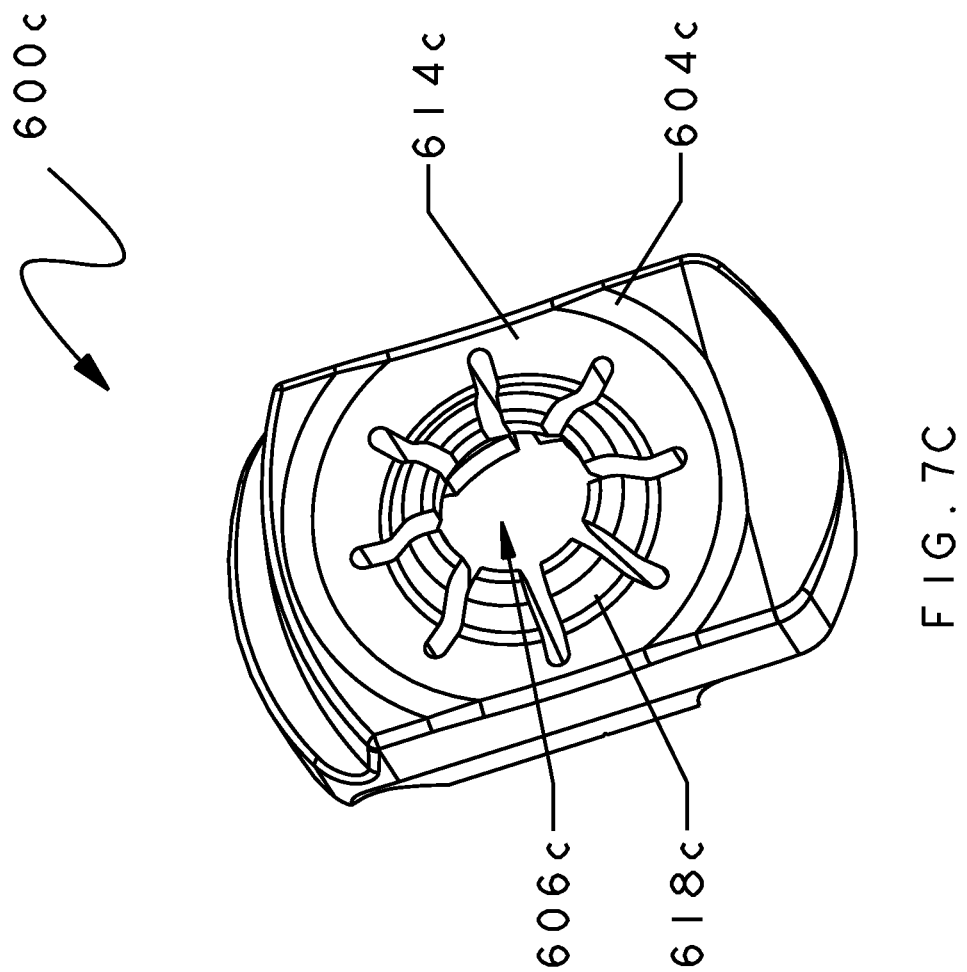

EXTERNAL FIXATION SYSTEM AND METHODS OF USE

INTRODUCTION

Clamp systems are used to fix the positions of fractured or broken bones during orthopedic surgeries. Typically, the clamp systems are secured to a support rod that extends from a fixed implement, such as a surgical table. The clamp system is be secured to a pin that is secured to the bone to fix a position of the bone. Holding the bone in a fixed position is desirable as the bone is set with one or more plates.

SUMMARY

In one aspect, the technology relates to a clamp system including: a first clamp at least partially defining a first jaw for receiving a support rod and a central opening; a second clamp at least partially defining a second jaw for receiving a pin and a central opening, wherein at least one of the first clamp and the second clamp includes a boss for rotatably positioning the first clamp relative to the second clamp; and a fixation rod received in the central openings of the first clamp and the second clamp for selectively securing a position of the first clamp relative to the second clamp. In another aspect, the technology relates to an external fixation system including: a fixation rod; a first clamp defining an opening for receiving the fixation rod; a second clamp defining an opening for receiving the fixation rod; a spacer disposed between the first clamp and the second clamp, wherein when the fixation rod is in a first position, the spacer is in an operable condition so as to maintain a distance between the first clamp and the second clamp so as to allow movement of the first clamp relative to the second clamp, and wherein when the fixation rod is in a second position, the spacer is in a permanently inoperable condition, wherein at least a portion of the first clamp is in contact with at least a portion of the second clamp. In another aspect, the technology relates to a method of using a clamp system, the method including: rotatably adjusting about an axis a position of a first clamp relative to a second clamp, wherein the axis is defined by a fixation rod; inserting at least one of a rod and a pin into the first clamp; moving the fixation rod to a fixed position, wherein when in the fixed position, a spacer element disposed between the first clamp and the second clamp is rendered permanently inoperable.

BRIEF DESCRIPTION OF THE DRAWINGS

There are shown in the drawings, embodiments which are presently preferred, it being understood, however, that the technology is not limited to the precise arrangements and instrumentalities shown.

FIGS. 1A and 1B depict perspective views of a fixation system.

FIGS. 3A and 3B depict interior and exterior perspective views, respectively, of a first clamp head.

FIGS. 4A and 4B depict interior and exterior perspective views, respectively, of a second clamp head.

FIG. 4C depicts an enlarged partial exterior perspective view of a second clamp head.

FIGS. 5A and 5B depict interior and exterior perspective views, respectively, of a third clamp head.

FIGS. 6A and 6B depict interior and exterior perspective views, respectively, of a fourth clamp head.

FIGS. 7A-7C depict exterior perspective views of alternative embodiments of third clamp heads.

DETAILED DESCRIPTION

Figure 8A:
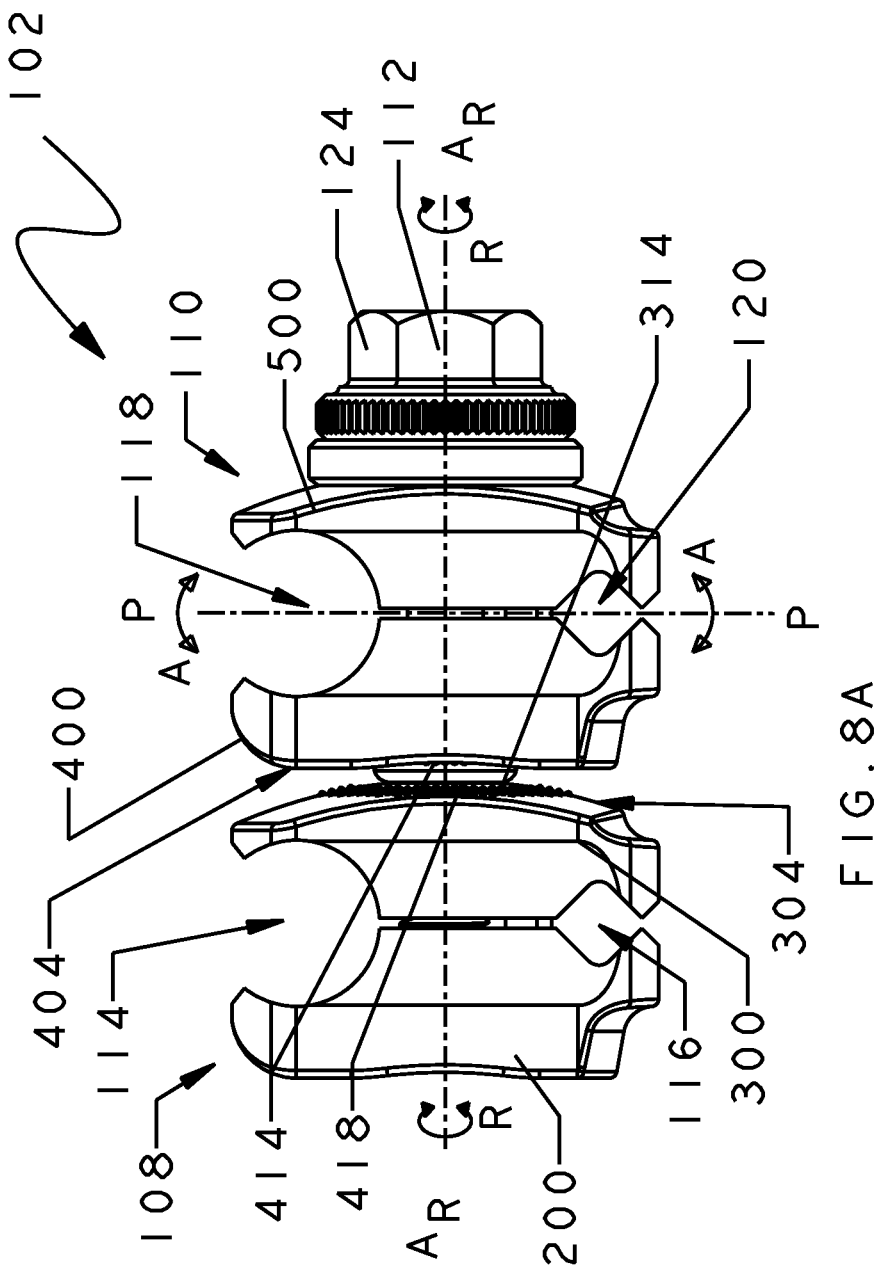
FIGS. 8A-8C depict side, top, and cross-sectional views, respectively, of a dual clamp fixation system in an adjustable condition.
Figure 8B:
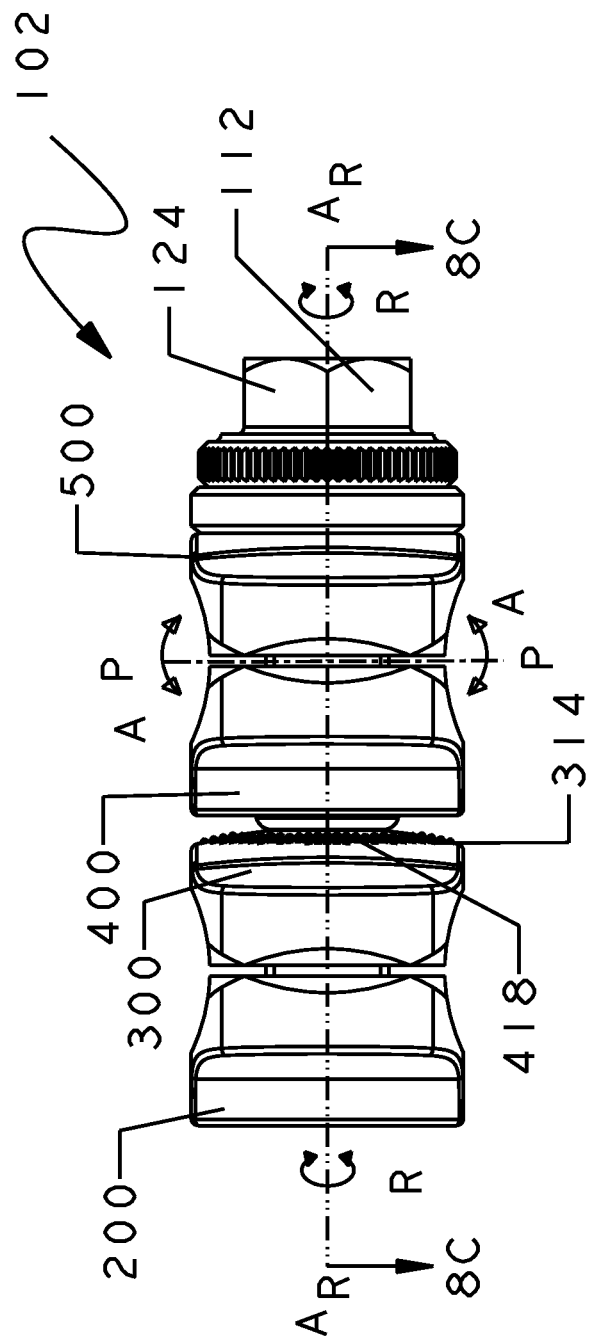

FIGS. 1A and 1B depict perspective views of a fixation system 100. The system 100 includes a dual clamp system 102. The dual clamp system 102 secures both support rods 104 and fixation pins 106 during surgical procedures, for example orthopedic surgeries that require positioning and/or placement of bone structures. The dual clamp system 102 includes two clamps 108, 110 that may be moved and positioned relative to each other. The clamps 108, 110 rotate R about a rod axis $A_R$ defined by a fixation rod 112. Additionally, the contours of the facing surfaces of the clamps 108, 110 allow the clamps 108, 110 to angulate relative to each other. Angulation is depicted in FIGS. 8A and 8B. Rotation and angulation of the clamps 108, 110 are possible when the fixation rod 112 is in a first, or loose, position. Once in a second, or fixed, position, the fixation rod 112 prevents movement of the clamps 108, 110, as described in more detail below.

Figure 2A:
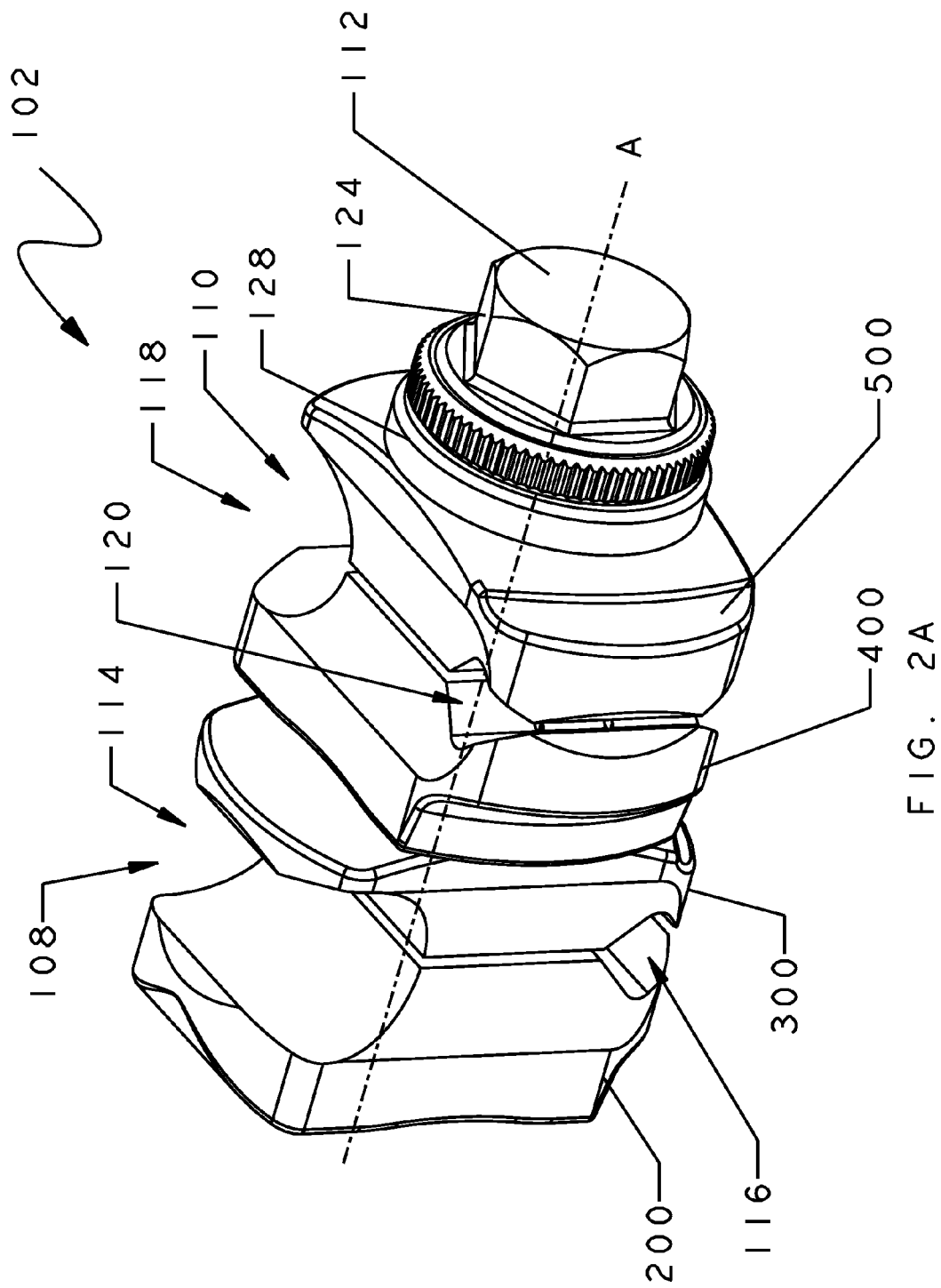
FIG. 2A depicts a perspective view of a dual clamp system utilized in a fixation system.
Figure 2B:
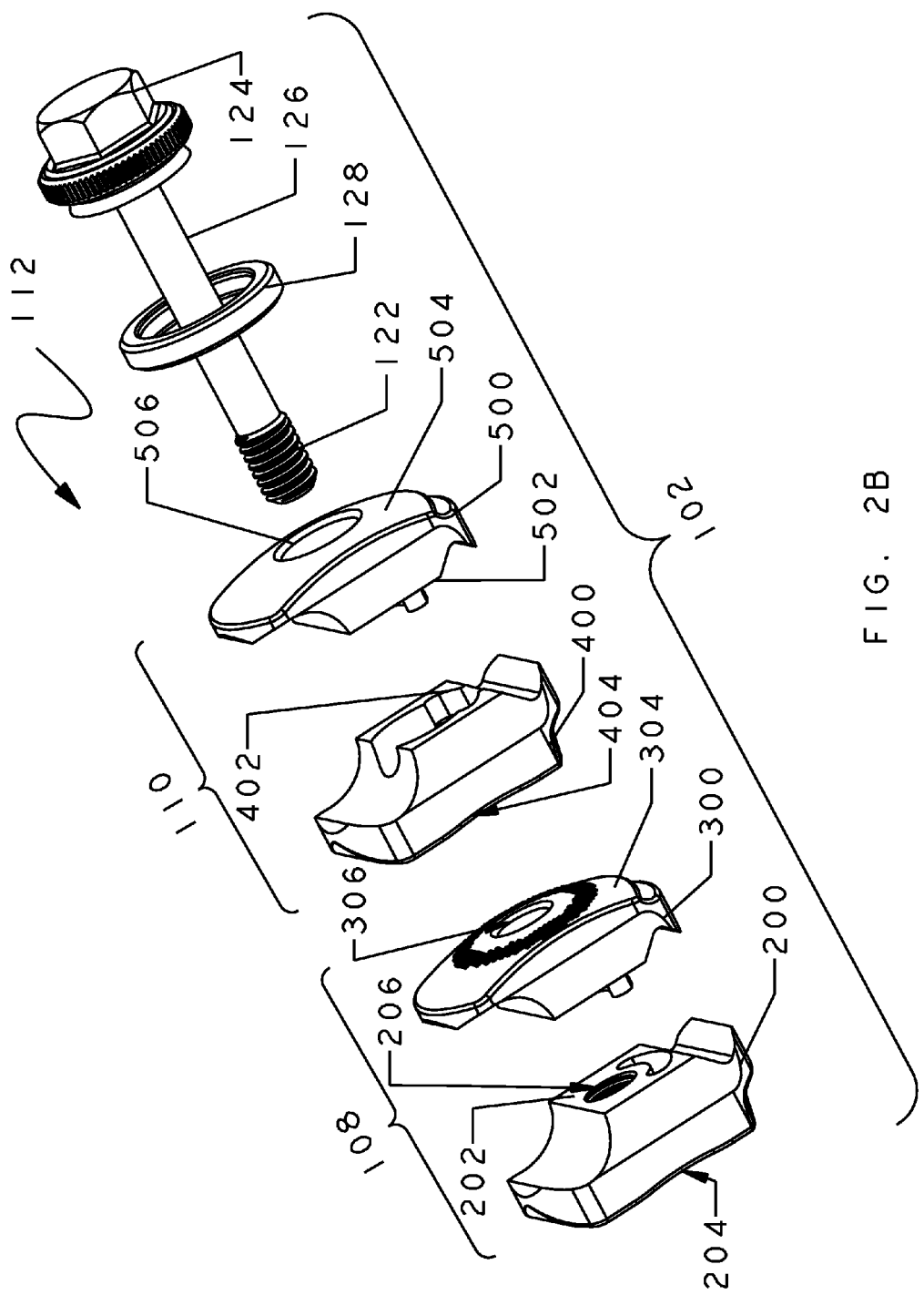
FIG. 2B depicts an exploded perspective view of the dual clamp system of FIG. 2A.

FIGS. 2A and 2B depict the dual clamp system 102 in assembled and exploded configurations, respectively. The dual clamp system 102 includes two clamps 108, 110, each of which are formed by two heads. The first clamp 108 includes a first head 200 and a second head 300. The two heads 200, 300 at least partially define both a rod jaw 114 and a pin jaw 116, for receipt of a rod and a pin, respectively. The first head 200 includes an interior surface 202 and an exterior surface 204, the configurations of which are described in more detail below. Similarly, the second head 300 includes an interior surface 302 and an exterior surface 304. The term "interior" is used to identify surfaces of the heads 200, 300 that face each other when the first clamp 108 is assembled. "Exterior" surfaces of each head 200, 300 face away from each other.

The second clamp 110 includes two heads, referred to as a third head 400 and a fourth head 500, for clarity. The two heads 400, 500 at least partially define both a rod jaw 118 and a pin jaw 120, for receipt of a rod and a pin, respectively. The third head 400 includes an interior surface 402 and an exterior surface 404, the configurations of which are described in more detail below. Similarly, the fourth head 500 includes an interior surface 502 and an exterior surface 504. As described above, the term "interior" is used to identify surfaces of the heads 400, 500 that face each other when the second clamp 110 is assembled. "Exterior" surfaces of each head 400, 500 face away from each other. The second head 300 and third head 400 interface at the exterior surfaces 304, 404, respectively. The function of these facing surfaces 304, 404 is described herein.

The dual clamp system 102 is supported by a fixation rod 112. As depicted in FIG. 2B, the fixation rod 112 includes a threaded end 122, an adjustment end 124, and a central portion 126 disposed therebetween. A washer may be disposed between the adjustment end 124 and the fourth head 500 to aid in fixing the position of the fixation rod 112. The threaded end 122 is configured to mate with matching threads in an opening 206 defined by the first head 200. The openings 306, 406, and 506 of the second 300, third 400, and fourth 500 heads are sized so as to permit movement between the respective head and the central portion 126 of the fixation rod 112. When the fixation rod 112 of the dual clamp system 102 is in the first position, the various heads and clamps may be adjusted relative to each other. For example, as described above, the two clamps 108, 110 may be rotated relative to each other about the axis $A_R$. Also as described above, the first clamp 108 and second clamp 110 may articulate relative to each other, due to the clamp structure disposed at the facing surfaces 304, 404. Additionally, each head of the two clamps 108, 110 may both pivot and separate relative to each other. For example, the first head 200 and second head 300 may pivot relative to each other within a predefined range of motion, limited by structures on the interior surfaces 202, 302, as described below. The first head 200 and second head 300 may also separate from each other (e.g., move apart generally along the axis $A_R$). This separation movement allows the jaws 114, 116 to be spread during insertion and removal of the rod or pin, respectively. The second clamp 110 has similarly movable heads 400, 500.

FIGS. 3A and 3B depict interior and exterior perspective views, respectively, of the first clamp head 200. As described above, the first head 200 defines a threaded opening 206 for receipt of a threaded end of a fixation rod. The opening 206 extends from the interior surface 202 to the exterior surface 204, but in other embodiments, the exterior surface need not define the opening, in which case, the threaded end of the fixation rod will not be visible once assembled. The interior surface 202 also defines a rod contour 208, which forms a part of the rod jaw 114, and a pin contour 210, which forms a part of the pin jaw 116. The interior surface 202 also defines a recess or channel 212, oriented radially from the opening 206. The channel 212 mates with a projection from the second head, described below, to limit the range of pivot between the first head 200 and the second head 300.

FIGS. 4A and 4B depict interior and exterior perspective views, respectively, of the second clamp head 300. The second head 300 defines an opening 306 for receipt of a central portion of the fixation rod. The opening 306 extends from the interior surface 302 to the exterior surface 304. The interior surface 302 also defines a rod contour 308, which forms a part of the rod jaw 114, and a pin contour 310, which forms a part of the pin jaw 116. The interior surface 302 also defines a radial projection 312. The projection 312 extends into the recess 212 on the first head 200 to limit the range of pivot between the first head 200 and the second head 300. The range of pivot between the first head 200 and second head 300 is based at least in part on the size of the recess 212 and the size of the projection 312 received therein. In certain embodiments, the total pivot range may be about 0 degrees to about 5 degrees, about 0 degrees to about 10 degrees, and about 0 degrees to about 15 degrees. The exterior surface 304 defines a generally convex shape that allows the first head 108 to articulate relative to the second head 108, as described in more detail below. At least a portion of the exterior surface 304 includes a texture 314. The texture 314 may be discreet projections, detents, radial ridges, or teeth. Alternatively, the texture 314 may be a portion of the exterior surface 304 that comprises a coefficient of friction higher than that of the exterior surface 304 itself, due to surface treatment, material, or other structure. FIG. 4C depicts a partial enlarged view of the exterior surface 304. Here, the texture 316 comprises a plurality of discrete raised projections 316 disposed on the exterior surface 304. In this embodiment, the projections 316 are pyramidal, but other shapes are contemplated. Exemplary projection shapes include a spherical cap, a hemisphere, a cone, a cylinder, a frustum, a torus, and a prism.

FIGS. 5A and 5B depict interior and exterior perspective views, respectively, of the third clamp head 400. The third head 400 defines an opening 406 for receipt of a central portion of the fixation rod. The opening 406 extends from the interior surface 402 to the exterior surface 404. The interior surface 402 also defines a rod contour 408, which forms a part of the rod jaw 118, and a pin contour 410, which forms a part of the pin jaw 120. The interior surface 402 also defines a recess or channel 412, oriented radially from the opening 406. The channel 412 mates with a projection from the fourth head, described below, to limit the range of pivot between the third head 400 and the fourth head 500. The exterior surface 404 defines a generally concave shape that allows the first head 108 to articulate relative to the second head 108. The convex exterior surface 304 of the second head 300 and the concave exterior surface 404 of the third head 400 function as a ball and socket joint, thus allowing for articulation between the two clamps 108, 110. At least a portion of the exterior surface 404 includes a texture 414. The texture 414 may similar to or different than the texture 314 on the second head 300, so as to engage when the clamp system is placed in the fixed condition.

The third head 400 also includes a raised boss, projection, or spacer 418 that projects above the exterior surface 404. In this embodiment, the boss 418 is in the shape of a ring that defines the opening 406. The boss 418 is cantilevered from the third head 400 with a lever 420. A top surface 422 of the boss 418 extends above the exterior surface 404 such that when the fixation rod is in a first position, the first clamp 108 may be moved (articulation and rotation) relative to the second clamp 110 without the two textured surfaces 314, 414 interfering with the movement. Thus, the boss 418 provides space between the second head 300 and the third head 400, such that contact between the textured surfaces 314, 414 is minimal or non-existent. Thus, movement of the first clamp 108 relative to the second clamp 110 may occur without locking engagement of the textured surfaces 314, 414. When the fixation rod is in the second position, the lever 420 and/or the boss 418 deforms into the plastic region of the material, or breaks, thus rendering the boss 418 permanently inoperable for spacing the first clamp 108 and the second clamp 110.

FIGS. 6A and 6B depict interior and exterior perspective views, respectively, of the fourth clamp head 500. The fourth head 500 defines an opening 506 for receipt of a central portion of the fixation rod. The opening 506 extends from the interior surface 502 to the exterior surface 504. The interior surface 502 also defines a rod contour 508, which forms a part of the rod jaw 118, and a pin contour 510, which forms a part of the pin jaw 120. The interior surface 502 also defines a radial projection 512. The projection 512 extends into the recess 412 on the third head to limit the range of pivot between the third head 400 and the fourth head 500. The range of pivot between the third head 400 and the fourth head 500 is based at least in part on the size of the recess 412 and the size of the projection 512 received therein. In certain embodiments, the total pivot range may be about 0 degrees to about 5 degrees, about 0 degrees to about 10 degrees, and about 0 degrees to about 15 degrees.

Figure 7A:
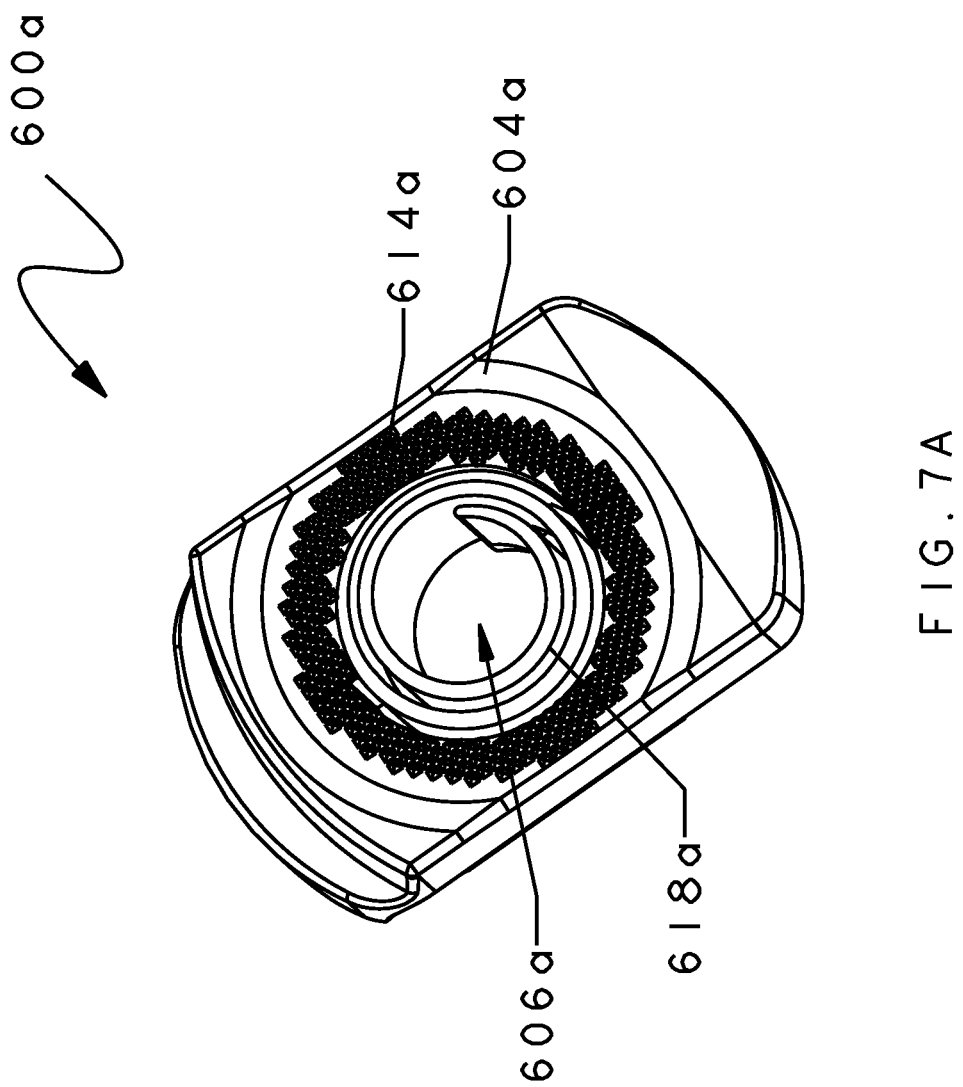

FIGS. 7A-7C depict exterior perspective views of alternative embodiments of third clamp heads 600a-600c. In general, the third clamp head 600 may include similar features and structures as the third clamp head 400 described above, accordingly, not all features have been labeled in these figures. Each of these alternative embodiments includes an exterior surface 604, as well as a texture 614 disposed thereon. A raised structure 618 surrounds the opening 606 and projects above the exterior surface 604 so as to space the third head 600 from the adjacent second head 300. In FIG. 7A, the structure 618a is in the form of a raised coil. In FIG. 7B, the structure 618b is in the form of a portion of a raised dome that has been modified to form a plurality of teeth. In FIG. 7C, the structure 618c is in the form of raised fingers. As with the boss 418 of previous embodiment, the structure 618 deforms into the plastic region of the material, or breaks, thus rendering the boss 418 inoperable for spacing the first clamp 108 and the second clamp 110 when the fixation rod 112 is set in a second position.

Figure 8C:
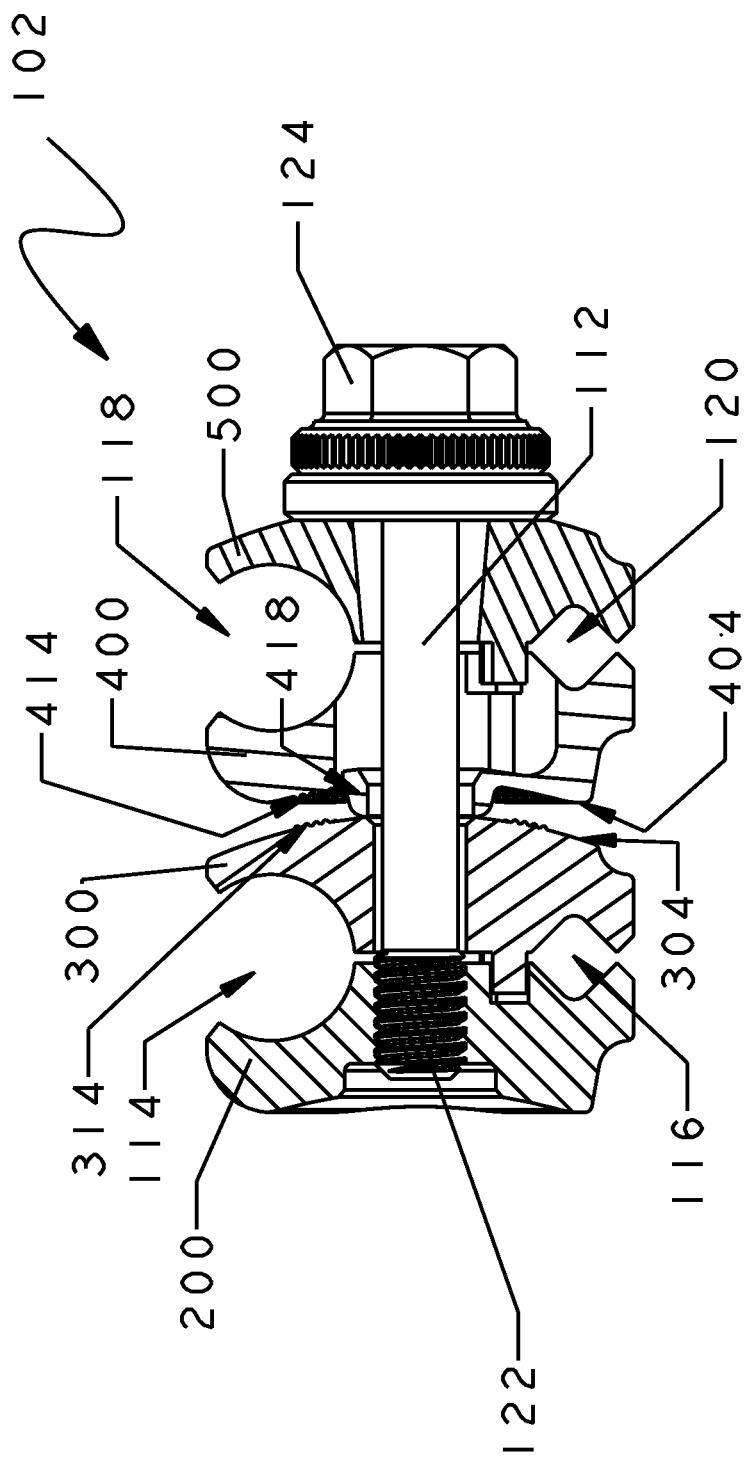

FIGS. 8A-8C depict side, top, and cross-sectional views, respectively, of a dual clamp fixation system 102 in an adjustable configuration. In the adjustable configuration, the fixation rod 112 is in a first position. In this first position, the boss 418 is disposed so as to provide space between the facing surfaces 304, 404 of the second head 300 and the third head 400. The space is sufficient to allow the first clamp 108 and second clamp 110 to be rotated R and angulated A relative to each other, without interference between the opposed textured surfaces 314, 414. Rotation R of the first clamp 108 relative to the second clamp 110 may be complete (that is, a full 360° about the rod axis $A_R$). Angulation A may be defined by movement of a plane defined by one of the clamps 108, 110. For example, FIGS. 8A and 8B depict a plane P that is defined by the second clamp 110. The plane P may be oriented orthogonally to the rod axis $A_R$. Angulation A may change the angle of intersection between the plane P and rod axis $A_R$ from about 0 degrees to about 5 degrees, about 0 degrees to about 10 degrees, and about 0 degrees to about 15 degrees. Thus, in this position, the position of the first clamp 108 and second clamp 110 may be adjusted, jaws 114-120 easily opened and closed, heads 200, 400 pivoted relative to their opposing head 300, 500, respectively. Other adjustments may also be made.

Figure 9A:
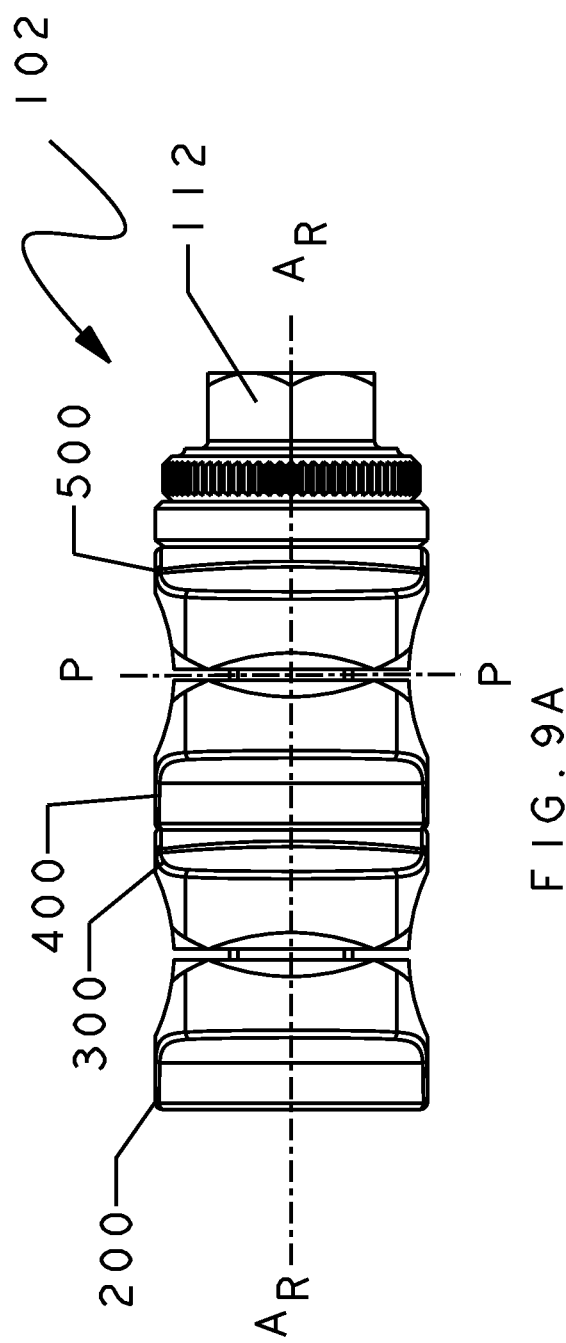
FIGS. 9A-9B depict top and cross-sectional views, respectively, of the dual clamp fixation system of FIG. 8A in an inoperable condition.
Figure 9B:
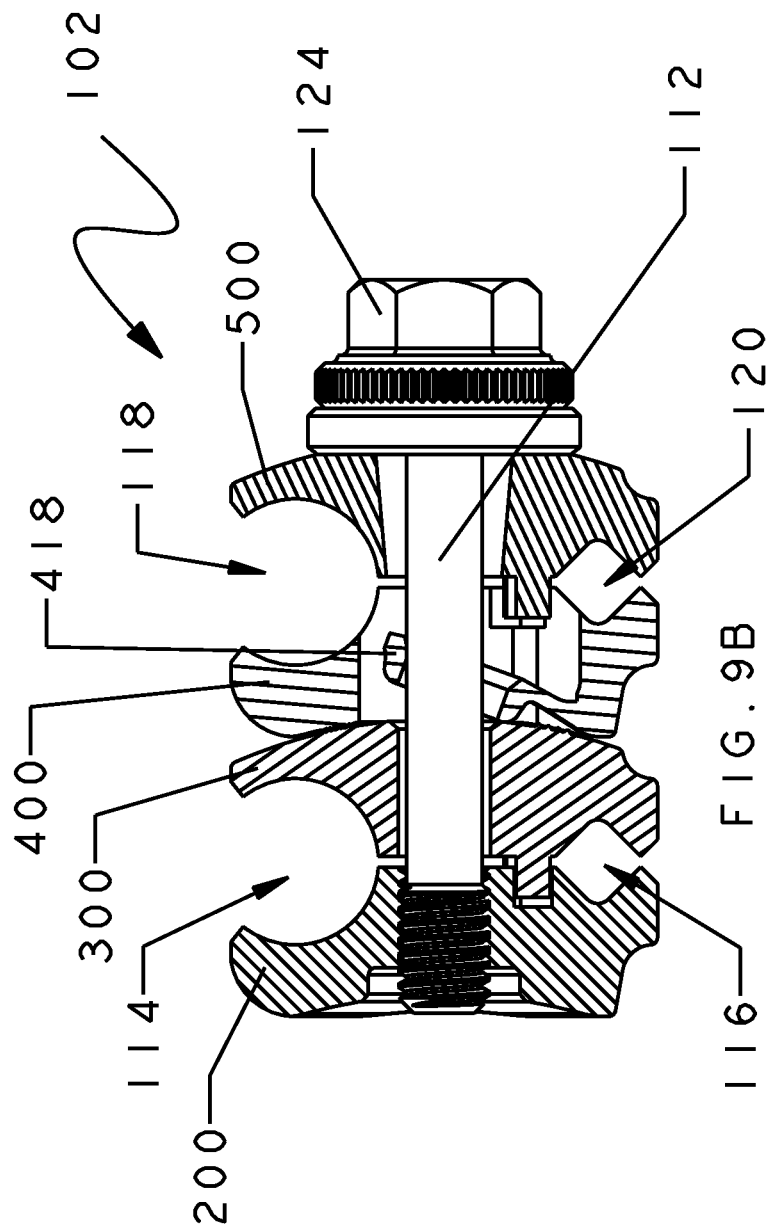

FIGS. 9A-9B depict top and cross-sectional views, respectively, of the dual clamp fixation system 102 of FIG. 8A in an inoperable configuration. In the inoperable configuration, the fixation rod 112 is in a second position. In this second position, the boss 418 has been forced into a region of plastic deformation. In alternative embodiments, the boss may be broken. Regardless, the boss 418 has been rendered permanently inoperable, such that when the fixation rod 112 is returned to the first position, the boss 418 will no longer provide spacing between the facing surfaces 304, 404 by having those surfaces 304, 404 away from each other. Also, in the inoperable configuration of FIGS. 9A-9B, the textured surfaces 314, 414 may be forced together so as to permanently damage those surfaces 314, 414. This damage, in addition to the deformation or breakage of the boss 418, prevents the dual clamp system 102 from being operated properly in the future. In this position, the position of the first clamp 108 and second clamp 110 is set and held fixed for the remainder of the surgical procedure. Although the plane P is depicted substantially orthogonal to the rod axis $A_R$, the clamps 108, 110 may be articulated relative to each other prior to fixing the position thereof by rotating the fixation rod 112. Similarly, either of the clamps 108, 110 may be rotated prior to fixation.

Figure 10:
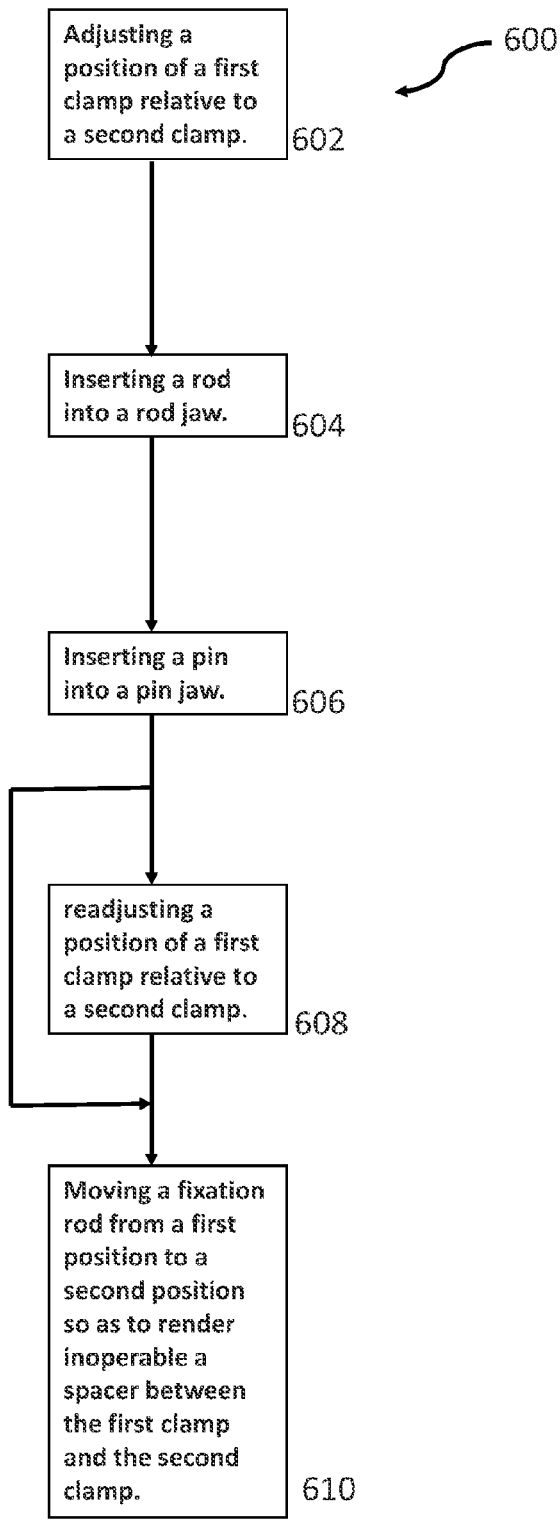
FIG. 10 depicts a method of utilizing a clamp system.

FIG. 10 depicts a method 600 of utilizing a clamp system. The method 600 may begin at operation 602, where a position of a first clamp relative to a second clamp may be adjusted. This step is optional become some users of the clamp system may wish to preposition the clamp system. Other users may choose to adjust a position of the clamp system only after a support rod is inserted into a rod jaw. A support rod may be inserted into a rod jaw of one of the first clamp and the second clamp in operation 604. A pin may be inserted into a pin jaw of one of the first clamp and the second clamp in operation 606. Operations 604 and 606 may be repeated for any number of rod jaws, pin jaws, and clamps. At any time during use, the position of the first clamp relative to the second clamp may be readjusted, as in operation 608. Since the clamp system is utilized during a surgical procedure that involves setting the position of a broken bone, rods and pins may be removed and inserted and clamp positions adjusted at any time during the procedure. When the clamp system has been positioned as required or desired, the fixation rod may be moved into a second position, which renders inoperable a spacer disposed between the first clamp and second clamp, as in operation 610.

Destruction of the boss or spacer renders the clamp system inoperable after a single use. Destruction of the clamp system is desirable since it eliminates the need to sterilize the clamp system after each use. Thus, a new, pre-sterilized clamp system must be used for each procedure. Rendering the clamp system inoperable may include one or more of: plastic deformation of the spacer or boss, breakage of the spacer or boss, deformation of a portion of the textured facing surfaces, and breakage of a portion of the textured facing surfaces. Deformation may be preferable to breakage, so as to reduce the risk of introduction of broken portions of the clamp into a surgical site. However, the clamp is configured so as to contain any broken components. To further ensure one-time use of the clamp system, a portion of the threaded end of the fixation rod that protrudes from the first head may be deformed after assembly, such that the clamp system cannot be disassembled. Damage may include crimping of the thread by mechanical means, welding the threads, or otherwise altering the threads such that the fixation rod may not be removed from the first head.

Other configurations of clamp systems are also contemplated. For example, a fixation rod may include a threaded end and fixed end having a shape that prevents rotation. In such an embodiment, the fixed end may be inserted into a similarly-shaped opening in one of the outer heads and the threaded end may be secured to a nut that may be tightened to lock the fixation rod. Additionally, each clamp may be manufactured as a single unitary element where two heads were connected by a flexible element. Additionally, clamps that form only a single rod jaw or a single pin jaw may be utilized, although clamps that form both jaws are more versatile. A clamp system may include a first clamp that forms only a rod jaw and a second clamp that forms only a pin jaw. Additionally, more than two clamps may be used if required or desired. In such an embodiment, it may be desirable to utilize a spacer as described above between each clamp.

The terms "first," "second," "third," "fourth," "interior," "exterior," and the like are relative terms used for clarity of the description only and are not intended to be limiting. For example, the boss 418, 618 depicted herein on the third head 400, 600 may instead be disposed on the second head 300. Additionally, the recesses 212, 412 defined by the first 200 and third 400 heads may instead be defined by the second 300 and fourth 500 heads. In such an embodiment, projections 312, 512 would have to be relocated to the opposite head. Additionally although it is advantageous to render the spacer 418, 618 permanently inoperable as described above, other embodiments that are not rendered permanently inoperable are also contemplated. In such embodiments, the bars or spacer would remain in the elastic range during use. Such a clamp system could be reused in multiple procedures.

Materials utilized in the manufacture of the clamp system may be those typically used in surgical equipment. Stainless steel, titanium, and other robust metals that may be sterilized may be used. Aluminum, anodized aluminum, and rigid polymers also may be utilized. Carbon fiber-reinforced polymers may be utilized, as they are lightweight, extremely strong, and may be sterilized. Of course, clamp systems utilizing a combination of materials may be used.

While there have been described herein what are to be considered exemplary and preferred embodiments of the present technology, other modifications of the technology will become apparent to those skilled in the art from the teachings herein. The particular methods of manufacture and geometries disclosed herein are exemplary in nature and are not to be considered limiting. It is therefore desired to be secured in the appended claims all such modifications as fall within the spirit and scope of the technology. Accordingly, what is desired to be secured by Letters Patent is the technology as defined and differentiated in the following claims, and all equivalents.

What is claimed is:

1. A clamp system comprising:
    a first clamp at least partially defining a first jaw for receiving a support rod and a central opening;
    a second clamp at least partially defining a second jaw for receiving a pin and a central opening,
    wherein at least one of the first clamp and the second clamp comprises a boss for rotatably positioning the first clamp relative to the second clamp, the boss including a plastically deformable material; and
    a fixation rod received in the central openings of the first clamp and the second clamp for selectively securing a position of the first clamp relative to the second clamp,
    wherein when the fixation rod is in a first position, the first clamp is rotatable relative to the second clamp; and
    wherein when the fixation rod is in a second position, the boss is in at least one of a plastically deformed condition and a broken condition.

2. The clamp system of claim 1, wherein:
    when the fixation rod is in a first position, the first clamp is rotatable relative to the second clamp.

3. The clamp system of claim 1, wherein the first clamp and the second clamp both comprise textured facing surfaces.

4. The clamp system of claim 3, wherein:
    when the fixation rod is in a first position, the textured facing surfaces are disengaged; and
    when the fixation rod is in a second position, the textured facing surfaces are engaged.

5. The clamp system of claim 1, wherein the first clamp and the second clamp each comprise two discrete heads, wherein each head defines an opening for receiving the fixation rod.

6. The clamp system of claim 5, wherein the fixation rod comprises a threaded end, and wherein at least one central opening defined by at least one head is threaded so as to mate with the threaded end.

7. The clamp system of claim 6, wherein the threaded end projects from the at least one threaded opening.

8. The clamp system of claim 6, wherein the fixation rod comprises an adjustment end opposite the threaded end.

9. The clamp system of claim 5, wherein the fixation rod is adapted to be connected to an adjustment nut.

10. The clamp system of claim 5, wherein a first head of the first clamp comprises a projection and wherein the second head of the first clamp defines a recess for receiving the projection, and wherein engagement between the projection and the recess limits a range of pivoting between the first head and the second head.

11. The clamp system of claim 5,
    wherein the first clamp comprises a first head and a second head, wherein the first head and the second head of the first clamp define a third jaw for receiving a pin; and
    wherein the second clamp defines a first head and a second head wherein the first head and the second head of the second clamp define a fourth jaw for receiving a rod.

12. An external fixation system comprising:
    a fixation rod;
    a first clamp defining an opening for receiving the fixation rod;
    a second clamp defining an opening for receiving the fixation rod; and
    a spacer disposed between the first clamp and the second clamp, the spacer including a plastically deformable material,
    wherein when the fixation rod is in a first position, the spacer is in an operable condition so as to maintain a distance between the first clamp and the second clamp so as to allow movement of the first clamp relative to the second clamp, and
    wherein when the fixation rod is in a second position, the spacer is in a permanently inoperable condition, wherein at least a portion of the first clamp is in contact with at least a portion of the second clamp.

13. The external fixation system of claim 12, wherein in the permanently inoperable condition, the spacer is at least one of plastically deformed and broken.

14. The external fixation system of claim 12, wherein the first clamp comprises a first opposing head and a second opposing head, wherein the first opposing head and the second opposing head together define a rod jaw and a pin jaw.

15. The external fixation system of claim 14, wherein at least one of the first opposing head and the second opposing head comprise a pivot-limiting device for limiting a pivot between the first opposing head and the second opposing head.

16. The external fixation system of claim 12, wherein the first clamp comprises a first surface and the second clamp comprises a second surface facing the first surface, and wherein at least one of the first surface and the second surface comprises a texture.

17. The external fixation system of claim 16, wherein when the fixation rod is in the second position, at least a portion of the texture is permanently deformed.

18. The external fixation system of claim 12, wherein the fixation rod comprises a threaded end adapted to be threadably received in one of:
    a threaded portion of at least one of the clamps; and
    a nut.

19. A clamp system comprising:
    a first clamp at least partially defining a first jaw for receiving a support rod and a central opening;

a second clamp at least partially defining a second jaw for receiving a pin and a central opening,
wherein at least one of the first clamp and the second clamp comprises a boss for rotatably positioning the first clamp relative to the second clamp, the boss including a plastically deformable material or a breakable material; and
a fixation rod received in the central openings of the first clamp and the second clamp for selectively securing a position of the first clamp relative to the second clamp,
wherein when the fixation rod is in a first position, the first clamp is rotatable relative to the second clamp,
wherein when the fixation rod is in a second position, the boss is in at least one of a plastically deformed condition and a broken condition, and
wherein the boss is permanently deformed when reaching the second position.

* * * * *